United States Patent
Maher et al.

(10) Patent No.: US 12,318,527 B2
(45) Date of Patent: Jun. 3, 2025

(54) CONTROL OF FLUID FLOW DURING PRIMING OF A FLUID FLOW CIRCUIT

(71) Applicant: Fenwal, Inc., Lake Zurich, IL (US)

(72) Inventors: Jeffrey R Maher, Schaumburg, IL (US); Jonathan W. Prendergast, Palatine, IL (US); Brian C. Case, Lake Villa, IL (US); Steven R Katz, Deerfield, IL (US); Robert Crampton, Gurnee, IL (US); Ryan DeLacey, Wheaton, IL (US)

(73) Assignee: Fenwal, Inc., Lake Zurich, IL (US)

( * ) Notice: Subject to any disclaimer, the term of this patent is extended or adjusted under 35 U.S.C. 154(b) by 185 days.

(21) Appl. No.: 17/888,546

(22) Filed: Aug. 16, 2022

(65) Prior Publication Data
US 2023/0055028 A1    Feb. 23, 2023

Related U.S. Application Data

(60) Provisional application No. 63/234,276, filed on Aug. 18, 2021.

(51) Int. Cl.
*A61M 1/36* (2006.01)
*A61M 1/02* (2006.01)
(Continued)

(52) U.S. Cl.
CPC ........ *A61M 1/3644* (2014.02); *A61M 1/0259* (2013.01); *A61M 60/113* (2021.01);
(Continued)

(58) Field of Classification Search
CPC ........ A61M 1/3643; A61M 2005/1402; A61M 1/288; A61M 1/3629
See application file for complete search history.

(56) References Cited

U.S. PATENT DOCUMENTS 4,120,449 A     10/1978   Brown et al.
4,828,545 A  *  5/1989   Epstein ............ A61M 5/14224
                                                        604/67
(Continued)

FOREIGN PATENT DOCUMENTS

EP          3034113 A1     6/2016
WO     WO-2021119401 A1 *  6/2021    ............ A61M 1/152

OTHER PUBLICATIONS

Extended European Search Report, dated Dec. 9, 2022, for application No. EP22190460.0-1113.

*Primary Examiner* — Adam Marcetich
*Assistant Examiner* — Ted Yang
(74) *Attorney, Agent, or Firm* — Cook Alex Ltd.

(57) ABSTRACT

A fluid processing system includes a fluid processing device and a fluid flow circuit. The device includes a pump configured to convey a priming fluid through the circuit. The pressure in a conduit of the circuit is measured while the pump is operated at a particular rate. When the magnitude of the pressure is less than the magnitude of a predetermined pressure at the end of a time interval, the pump is operated at an increased rate. When the magnitude of the pressure is greater than the magnitude of the predetermined pressure at the end of the time interval, the pump is instead operated at a decreased rate. The magnitude of the pressure in the conduit is again compared to the magnitude of the predetermined pressure after the pump has operated at the increased or decreased rate for the time interval to determine how to next adjust the operational rate.

20 Claims, 7 Drawing Sheets

(51) Int. Cl.
*A61M 60/113* (2021.01)
*A61M 60/279* (2021.01)
*A61M 60/39* (2021.01)
*A61M 60/554* (2021.01)

(52) U.S. Cl.
CPC .......... *A61M 60/279* (2021.01); *A61M 60/39* (2021.01); *A61M 60/554* (2021.01); *A61M 1/0272* (2013.01); *A61M 2205/3331* (2013.01)

(56) References Cited

U.S. PATENT DOCUMENTS

| | | | |
|---|---|---|---|
| 5,316,667 | A | 5/1994 | Brown et al. |
| 10,561,784 | B2 | 2/2020 | Katz et al. |
| 10,842,929 | B2 | 11/2020 | West |
| 2010/0191164 | A1* | 7/2010 | Sasaki ................ A61M 1/3607 604/5.04 |
| 2012/0273354 | A1* | 11/2012 | Orhan ................ A61M 1/284 204/627 |
| 2013/0274642 | A1* | 10/2013 | Soykan ................ A61B 5/145 210/645 |
| 2013/0317837 | A1* | 11/2013 | Ballantyne ............ G06F 1/1626 705/2 |
| 2014/0045668 | A1 | 2/2014 | Case et al. |
| 2014/0100507 | A1* | 4/2014 | Flexman ................ A61M 1/38 210/696 |
| 2016/0175510 | A1* | 6/2016 | Patel ................ A61M 5/16854 137/12 |
| 2017/0224899 | A1* | 8/2017 | Wojke ................ A61M 1/3643 |
| 2019/0262526 | A1* | 8/2019 | Wyeth ................ A61M 1/154 |
| 2020/0061281 | A1* | 2/2020 | Desouza ............ A61M 1/1601 |
| 2020/0316283 | A1* | 10/2020 | Vecten ................ A61M 1/1621 |
| 2022/0203004 | A1* | 6/2022 | Hu ...................... A61M 1/3643 |
| 2023/0019233 | A1* | 1/2023 | Jensen ................ A61M 1/152 |
| 2023/0211059 | A1* | 7/2023 | Treu .................... A61M 1/3646 604/6.09 |
| 2023/0355854 | A1* | 11/2023 | Ahmadi ................ A61M 1/3626 |

\* cited by examiner ns and
methods. More particularly, the disclosure relates to systems
and methods for controlling fluid flow during priming of a
fluid flow circuit mounted to a fluid processing device.

CONTROL OF FLUID FLOW DURING PRIMING OF A FLUID FLOW CIRCUIT

CROSS-REFERENCE TO RELATED APPLICATIONS

This application claims the benefit of and priority of U.S. Provisional Patent Application Ser. No. 63/234,276, filed Aug. 18, 2021, the contents of which are incorporated by reference herein.

BACKGROUND

Field of the Disclosure

The disclosure relates to fluid processing systems and methods. More particularly, the disclosure relates to systems and methods for controlling fluid flow during priming of a fluid flow circuit mounted to a fluid processing device.

Description of Related Art

Various blood processing systems now make it possible to collect particular blood constituents, rather than whole blood, from a blood source. Typically, in such systems, whole blood is drawn from a blood source, the particular blood component or constituent is separated, removed, and collected, and the remaining blood constituents are returned to the blood source. Removing only particular constituents is advantageous when the blood source is a human donor or patient, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents through centrifugation. This requires that the whole blood be passed through a centrifuge after it is withdrawn from, and before it is returned to, the blood source. To avoid contamination and possible infection (if the blood source is a human donor or patient), the blood is preferably contained within a sealed, sterile fluid flow system during the entire centrifugation process. Typical blood processing systems thus include a permanent, reusable assembly containing the hardware (centrifuge, drive system, pumps, valve actuators, programmable controller, and the like) that spins and pumps the blood, and a disposable, sealed, and sterile flow circuit that is mounted in cooperation on the hardware.

The centrifuge engages and spins the disposable flow circuit during a blood separation step. As the flow circuit is spun by the centrifuge, the heavier (greater specific gravity) components of the whole blood in the flow circuit, such as red blood cells, move radially outwardly away from the center of rotation toward the outer or "high-G" wall of the centrifuge. The lighter (lower specific gravity) components, such as plasma, migrate toward the inner or "low-G" wall of the centrifuge. Various ones of these components can be selectively removed from the whole blood by providing appropriately located channeling seals and outlet ports in the flow circuit. For example, in one blood separation procedure, plasma is separated from cellular blood components and collected, with the cellular blood components and a replacement fluid being returned to the blood source.

According to one known design, the centrifuge may be rotated about a rotational axis by an umbilicus. Umbilicus-driven centrifuges have been known since the 1970s, as described in U.S. Pat. No. 4,120,449, which is hereby incorporated herein by reference. In an umbilicus-based system, the centrifuge is connected to a first end of an umbilicus, while the opposite end of the umbilicus is spaced from the first end along the rotational axis of the centrifuge. The first end of the umbilicus is free to twist and rotate with the centrifuge, while the opposite end is held in place without rotating or twisting. A section of the umbilicus between its ends is orbited around the centrifuge by a yoke. The yoke and associated section of the umbilicus orbit around the rotational axis of the centrifuge at a speed that is commonly referred to as "one omega."

Due to one end of the umbilicus being fixed in place, the umbilicus tends to become twisted about its central axis as its central section is orbited about the rotational axis of the centrifuge by the yoke. However, the material composition of the umbilicus is such that it untwists itself, rather than kinking or otherwise becoming inoperative. This has the effect of increasing the rate at which the centrifuge spins, because the free end of the umbilicus (to which it is secured) is the only end of the umbilicus that may untwist to oppose the tendency of the umbilicus to become twisted. The yoke being rotated to orbit the central section of the umbilicus around the rotational axis of the centrifuge at the "one omega" speed combines with the action of the umbilicus to untwist about its own central axis to impart a "two omega" average rotational speed to the bowl and spool of the centrifuge, which is twice the "one omega" rotational speed of the yoke.

The status of fluid being separated in the centrifuge (namely, in the disposable flow circuit mounted within the centrifuge) is monitored by an optical monitoring system. According to one known approach, an optical monitoring system is mounted onto the yoke and, thus, rotates at the "one omega" speed, as described in U.S. Pat. No. 5,316,667, which is hereby incorporated herein by reference. According to an alternative approach, the optical monitoring system may be mounted to a stationary radial location, as described in U.S. Patent No, 2014/0045668, which is hereby incorporated herein by reference.

Prior to any blood processing, the disposable flow circuit mounted to the hardware must be primed in order to clear air from the various conduits and components of the circuit. To prime the circuit, a priming fluid (which is typically saline or anticoagulant or some other non-biological fluid, but may be a biological fluid, such as blood) is pumped through the circuit to force the air to one or more suitable locations within the circuit, such as a waste bag or container. Once the air has been cleared to a suitable location or locations within the circuit, blood processing may begin.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fluid processing device configured for use in combination with a fluid flow circuit includes a pump, a pressure sensor, and a controller. The controller is configured to execute a priming procedure in which it controls the pump to operate at a current rate for a predetermined time interval to convey a priming fluid through at least a portion of a fluid flow circuit. The pressure sensor is controlled to measure a pressure in a conduit of the fluid flow circuit, with the controller comparing the magnitude of the pressure to the magnitude of a predetermined pressure at the end of the predetermined time interval. When the magnitude of the pressure is less than the magnitude of the predetermined pressure at the end of the predetermined time interval, the pump is controlled to operate at an increased rate that is greater than the current rate. When the magnitude of the pressure is not less than the magnitude of the predetermined pressure at the end of the predetermined time interval, the pump is controlled to operate at a decreased rate that is less than the current rate. When the pump has not previously been operated during the priming procedure at a previous rate at which the magnitude of the pressure was less than the magnitude of the predetermined pressure at the end of a previous time interval during which the pump was operated at said previous rate, the decreased rate is equal to a predetermined safe rate. When the pump has previously been operated during the priming procedure at at least one previous rate at which the magnitude of the pressure was less than the magnitude of the predetermined pressure at the end of a previous time interval during which the pump was operated at said at least one previous rate, the decreased rate is equal to the previous rate at which the pump most recently operated at which the magnitude of the pressure was less than the magnitude of the predetermined pressure at the end of said previous time interval during which the pump was operated at said at least one previous rate during the priming procedure.

In another aspect, a method is provided for executing a priming procedure in which a pump of a fluid processing device is operated to convey a priming fluid through at least a portion of a conduit. The method includes operating the pump at a current rate for a predetermined time interval to convey the priming fluid through said at least a portion of the conduit. Pressure in the conduit is measured with the magnitude of the pressure being compared to the magnitude of a predetermined pressure at the end of the predetermined time interval. When the magnitude of the pressure is less than the magnitude of the predetermined pressure at the end of the predetermined time interval, the pump is operated at an increased rate that is greater than the current rate.

When the magnitude of the pressure is not less than the magnitude of the predetermined pressure at the end of the predetermined time interval, the pump is operated at a decreased rate that is less than the current rate. When the pump has not previously been operated during the priming procedure at a previous rate at which the magnitude of the pressure was less than the magnitude of the predetermined pressure at the end of a previous time interval during which the pump was operated at said previous rate, the decreased rate is equal to a predetermined safe rate. When the pump has previously been operated during the priming procedure at at least one previous rate at which the magnitude of the pressure was less than the magnitude of the predetermined pressure at the end of a previous time interval during which the pump was operated at said at least one previous rate, the decreased rate is equal to the previous rate at which the pump most recently operated at which the magnitude of the pressure was less than the magnitude of the predetermined pressure at the end of said previous time interval during which the pump was operated at said at least one previous rate during the priming procedure.

In yet another aspect, a fluid processing device configured for use in combination with a fluid flow circuit includes a pump, a pressure sensor, and a controller. The controller is configured to execute a priming procedure in which it controls the pump to operate at a current rate for a predetermined time interval to convey a priming fluid through at least a portion of a fluid flow circuit. The pressure sensor is controlled to measure a pressure in a conduit of the fluid flow circuit, with the controller comparing the magnitude of the pressure to the magnitude of a predetermined pressure at the end of the predetermined time interval. When the magnitude of the pressure is greater than the magnitude of the predetermined pressure at the end of the predetermined time interval, the pump is controlled to operate at an increased rate that is greater than the current rate. When the magnitude of the pressure is not greater than the magnitude of the predetermined pressure at the end of the predetermined time interval, the pump is controlled to operate at a decreased rate that is less than the current rate. When the pump has not previously been operated during the priming procedure at a previous rate at which the magnitude of the pressure was greater than the magnitude of the predetermined pressure at the end of a previous time interval during which the pump was operated at said previous rate, the decreased rate is equal to a predetermined safe rate. When the pump has previously been operated during the priming procedure at at least one previous rate at which the magnitude of the pressure was greater than the magnitude of the predetermined pressure at the end of a previous time interval during which the pump was operated at said at least one previous rate, the decreased rate is equal to the previous rate at which the pump most recently operated at which the magnitude of the pressure was greater than the magnitude of the predetermined pressure at the end of said previous time interval during which the pump was operated at said at least one previous rate during the priming procedure.

In another aspect, a method is provided for executing a priming procedure in which a pump of a fluid processing device is operated to convey a priming fluid through at least a portion of a conduit. The method includes operating the pump at a current rate for a predetermined time interval to convey the priming fluid through said at least a portion of the conduit. Pressure in the conduit is measured with the magnitude of the pressure being compared to the magnitude of a predetermined pressure at the end of the predetermined time interval. When the magnitude of the pressure is greater than the magnitude of the predetermined pressure at the end of the predetermined time interval, the pump is operated at an increased rate that is greater than the current rate. When the magnitude of the pressure is not greater than the magnitude of the predetermined pressure at the end of the predetermined time interval, the pump is operated at a decreased rate that is less than the current rate. When the pump has not previously been operated during the priming procedure at a previous rate at which the magnitude of the pressure was greater than the magnitude of the predetermined pressure at the end of a previous time interval during which the pump was operated at said previous rate, the decreased rate is equal to a predetermined safe rate. When the pump has previously been operated during the priming procedure at at least one previous rate at which the magnitude of the pressure was greater than the magnitude of the predetermined pressure at the end of a previous time interval during which the pump was operated at said at least one previous rate, the decreased rate is equal to the previous rate at which the pump most recently operated at which the magnitude of the pressure was greater than the magnitude of the predetermined pressure at the end of said previous time interval during which the pump was operated at said at least one previous rate during the priming procedure.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
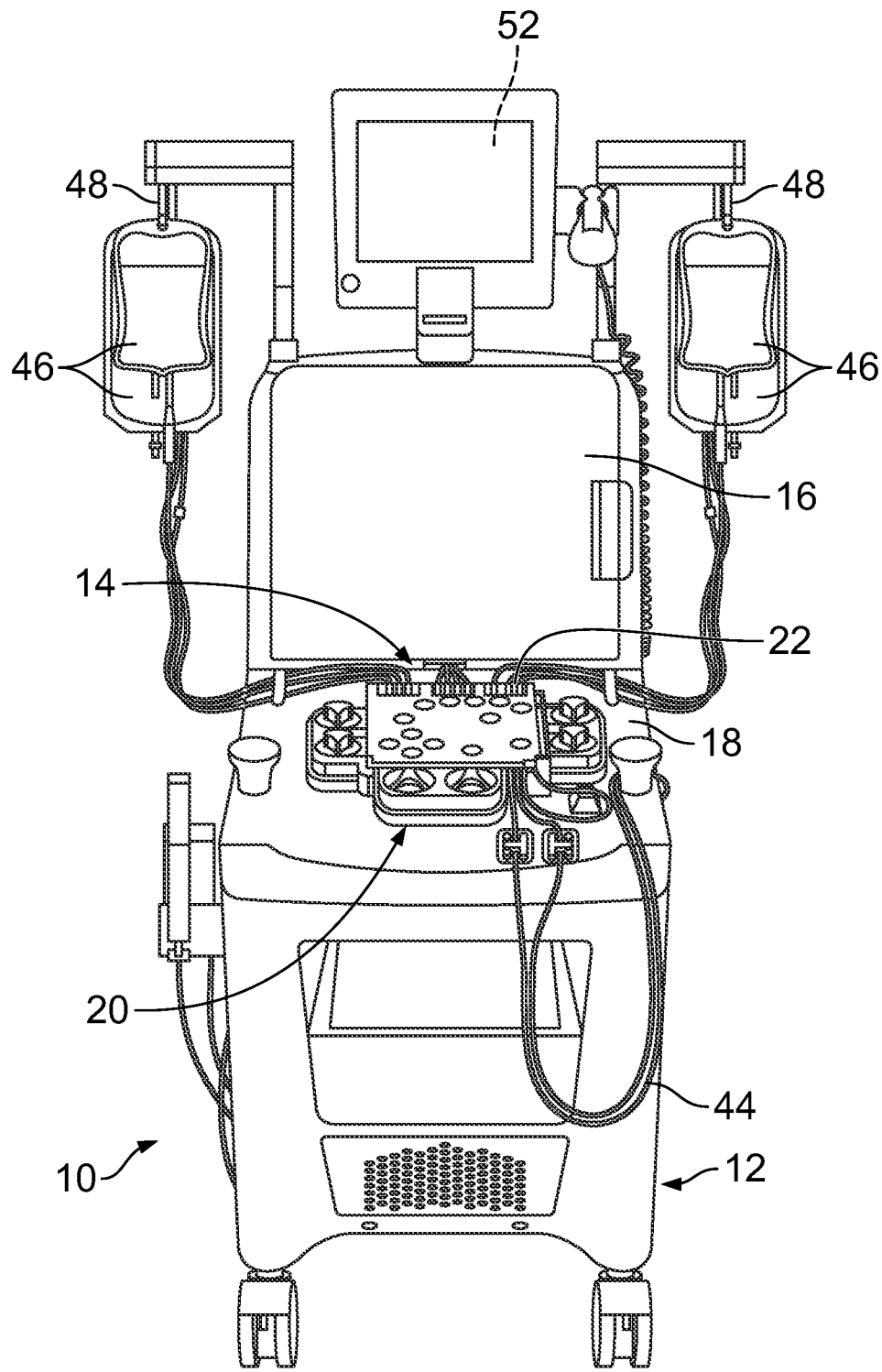
FIG. 1 is a front elevational view of an exemplary fluid processing system according to an aspect of the present disclosure.

FIG. 1 shows an exemplary fluid processing system 10 that can be used for processing various fluids, but may be particularly well suited for processing whole blood and other suspensions of biological cellular materials. The illustrated system 10 includes a reusable or durable component 12 (referred to herein as a "fluid processing device" and shown in FIG. 2) and a disposable or single-use component 14 (referred to herein as a "fluid processing circuit" and shown in FIG. 3). While flow control principles will be described herein with reference to one particular system 10, it should be understood that these principles may be employed with other fluid processing systems and devices without departing from the scope of the present disclosure.

Figure 2:
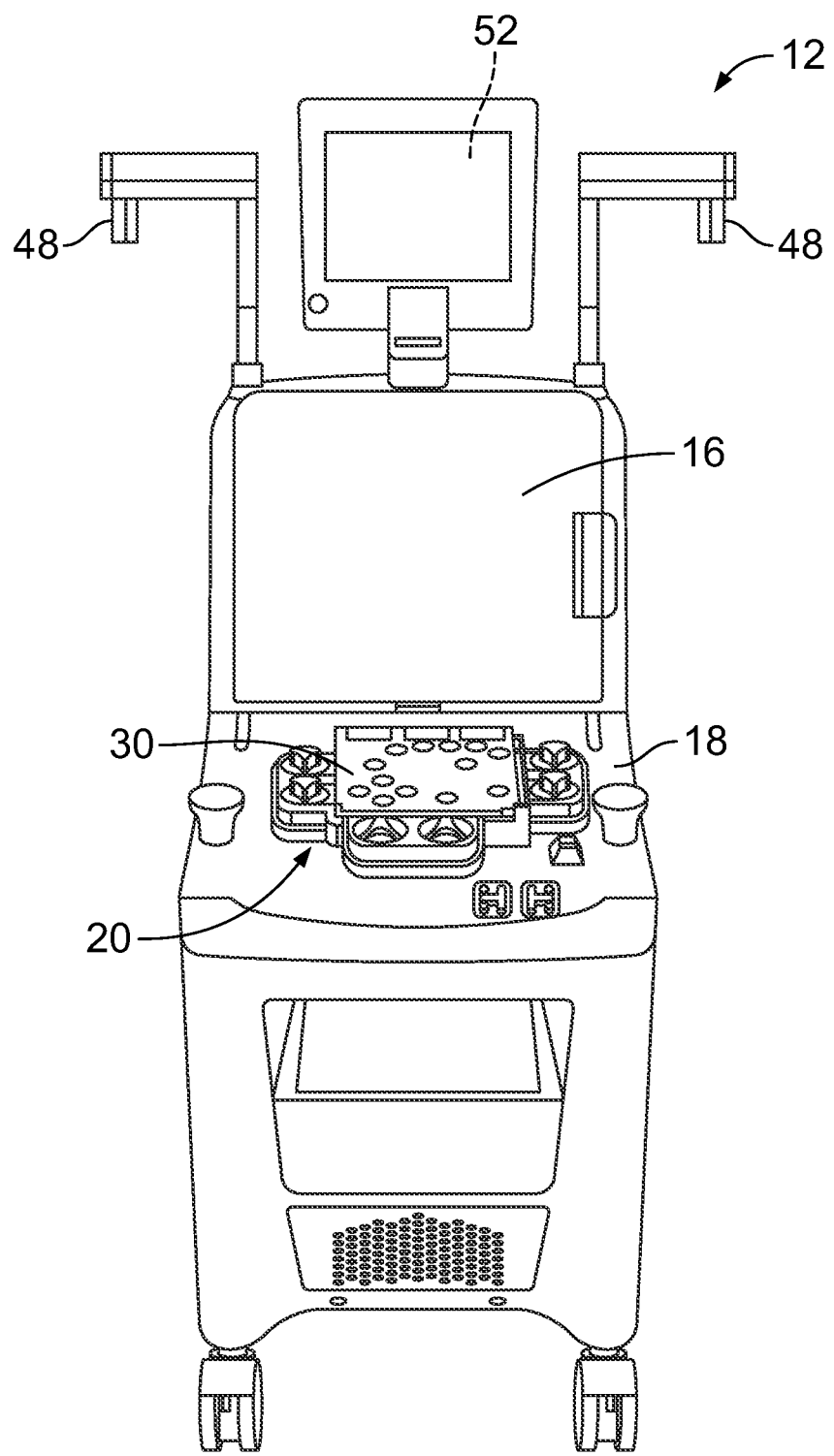
FIG. 2 is a front elevational view of a fluid processing device of the fluid processing system of FIG. 1.

The fluid processing device 12 may be variously configured without departing from the scope of the present disclosure, with the fluid processing device 12 shown in FIGS. 1 and 2 being provided generally in accordance with the system currently marketed as the AmiCORE apheresis device by Fenwal, Inc. of Lake Zurich, Illinois, which is an affiliate of Fresenius Kabi AG of Bad Homburg, Germany. Depending on the configuration of the fluid processing device 12, it may be capable of executing any of a number of different procedures in which a fluid (whether biological or non-biological) is processed, which may include the separation of a fluid into two or more components when the fluid processing device 12 is provided with a suitable separator, such as a centrifuge or a spinning membrane separator. For example, the illustrated fluid processing device 12 includes a centrifuge (not visible) that is accessible via a front door 16.

The illustrated device 12 further includes a sloped front panel 18 having a loading area or cassette holder 20 (FIGS. 4 and 5), which is configured to receive and grip a cassette 22 (FIGS. 5 and 6) of the fluid flow circuit 14. It should be understood that the fluid flow circuit 14 (including the cassette 22, if provided) will be particularly configured to cooperate with the associated fluid processing device 12, such that the configuration of the fluid flow circuit 14 will vary along with the configuration of the fluid processing device 12.

The illustrated cassette 22 includes an injection molded body 24 that is compartmentalized to form a plurality of defined pathways. The body 24 may be covered by a top cover and a bottom cover (which are omitted from FIGS. 5 and 6 to better illustrate the configuration of the body 24), enabling the cassette 22 and its fluid contents to be closed from the surrounding environment. For the purposes of description, the side of the cassette 22 facing away from the cassette holder 20 in use is considered to be the top of the cassette 22 (FIG. 5), while the opposing, bottom surface of the cassette 22 (FIG. 6) faces towards the cassette holder 20. In one embodiment, the cassette body 24 and the top cover are formed of a rigid, medical grade material (e.g., a rigid plastic material), while the bottom cover is configured as a diaphragm or membrane formed of a flexible sheet of medical grade material (e.g., a flexible plastic material).

Figure 6:
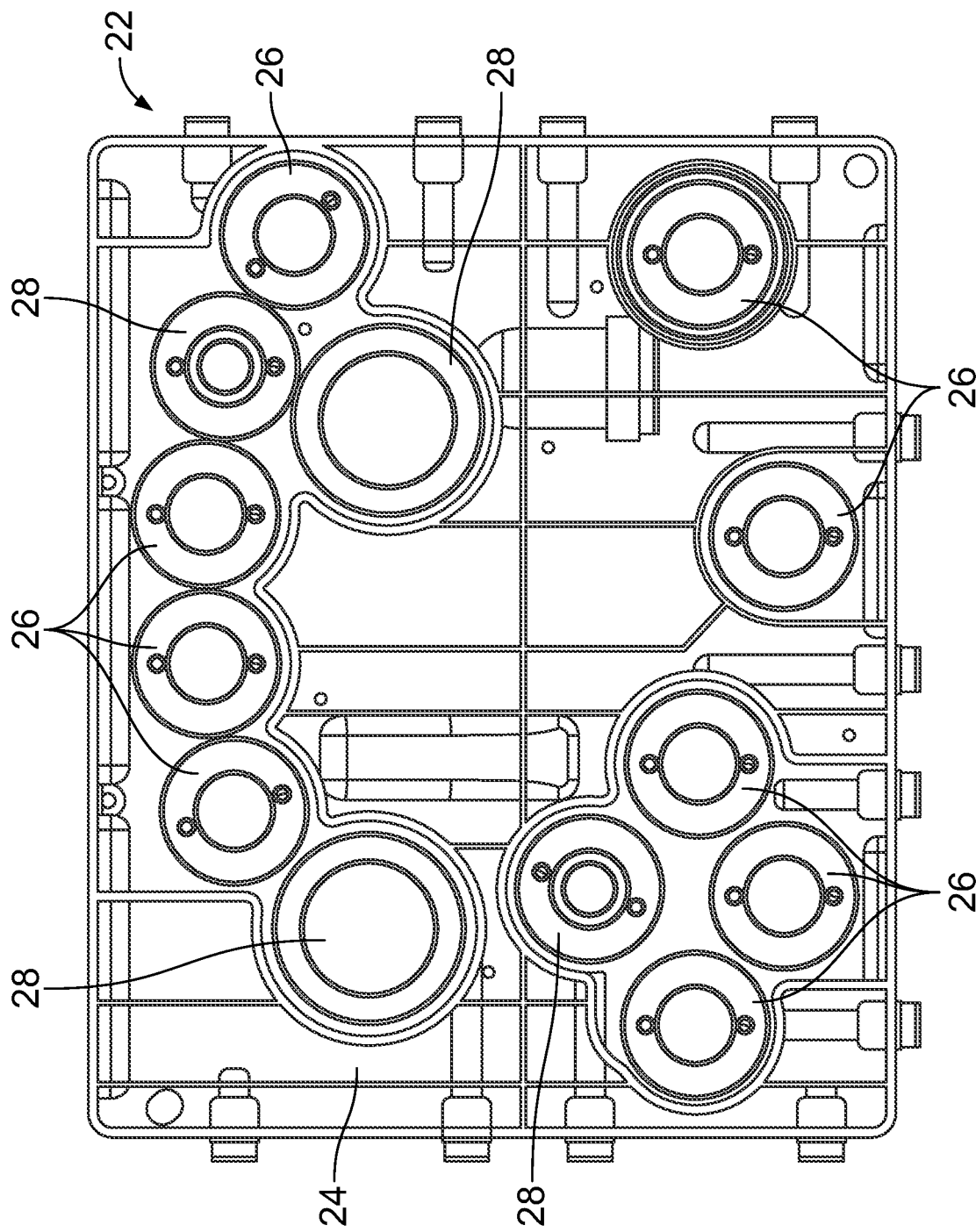
FIG. 6 is a bottom plan view of the cassette of FIG. 5.

As shown in FIG. 6, the bottom of the cassette body 24 may include an array of valve stations 26 disposed under and/or adjacent to certain locations of the various defined pathways of the body 24. The bottom of the cassette body 24 may also define a plurality of pressure-sensing stations 28. The valve stations 26 and the pressure-sensing stations 28 may communicate with the various defined pathways in a predetermined manner. The number, configuration, and/or arrangement of the valve stations 26 and the sensing stations 28 may vary without departing from the scope of the present disclosure.

Figure 4:
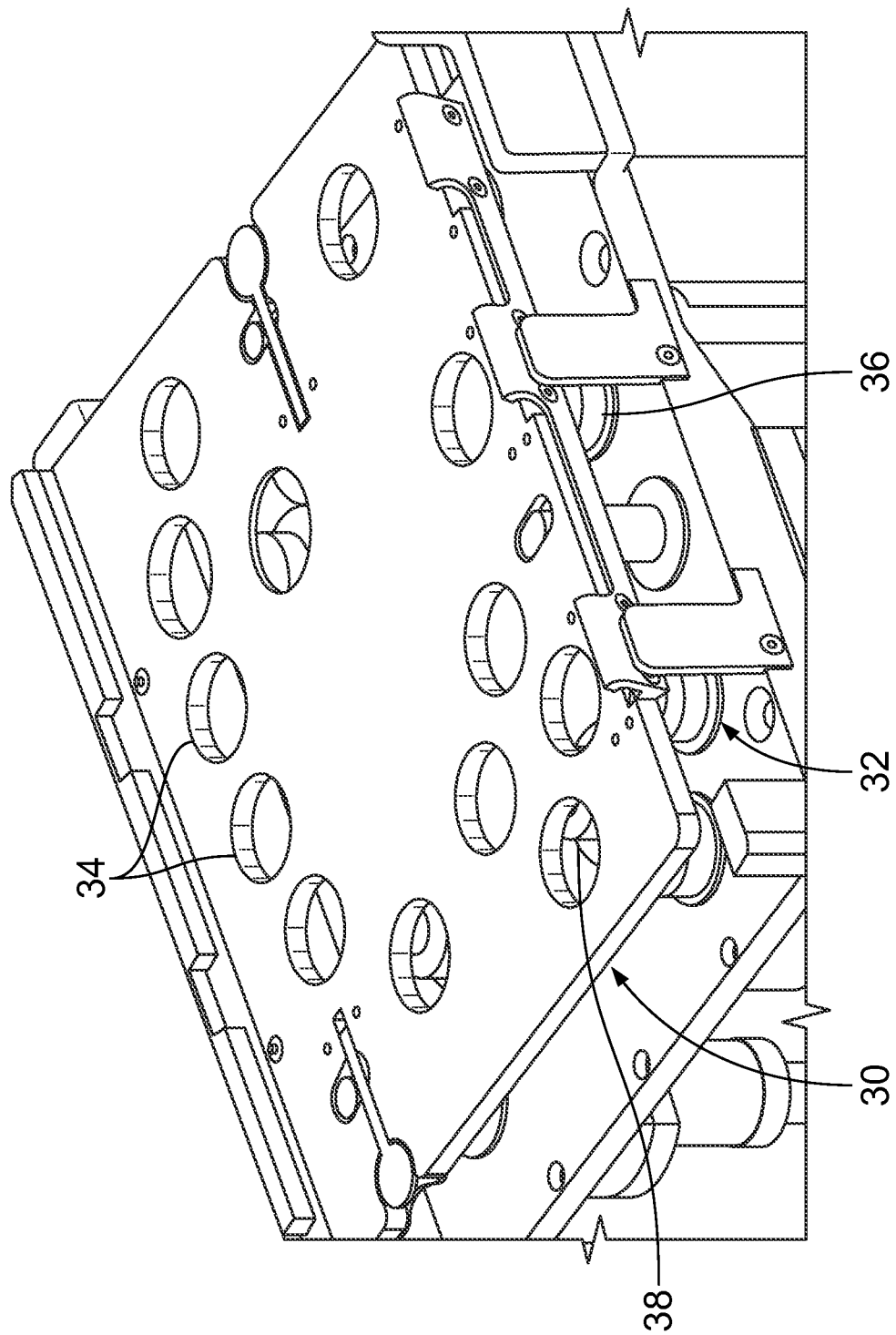
FIG. 4 is a top perspective view of a portion of a cassette holder of the fluid processing device of FIG. 2.
Figure 5:
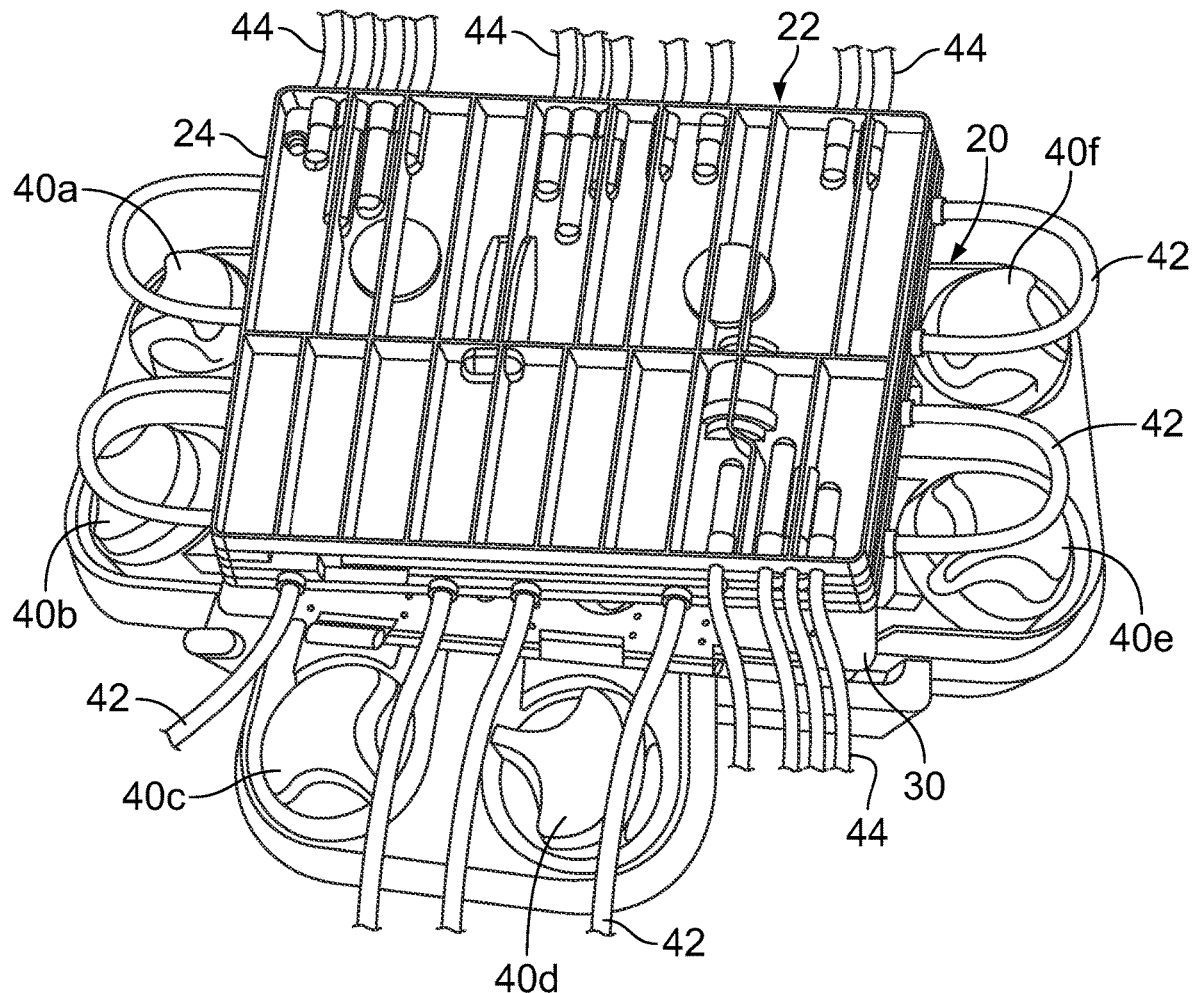
FIG. 5 is a top perspective view of a cassette of the fluid flow circuit of FIG. 3 prior to being mounted to the cassette holder of FIG. 4.

The cassette holder 20 is configured to receive and grip the cassette 22 in a desired operating position, with the cassette 22 seated upon a cassette plate 30 of the cassette holder 20, which can be seen in FIGS. 4 and 5. A suitable cassette holder 20 and cassette plate 30 are shown and described in greater detail in U.S. Pat. No. 10,842,929, which is hereby incorporated herein by reference.

The cassette holder 20 may be configured such that, when the cassette 22 has been loaded onto the cassette plate 30, the cassette holder 20 lowers the cassette 22 into contact with a valve and sensor assembly 32 of the cassette holder 20 (FIG. 4) located underneath the cassette plate 30. The cassette plate 30 may define a plurality of openings 34 to allow components of the valve and sensor assembly 32 to access the valve stations 26 and sensing stations 28 of the cassette 22 when the cassette 22 and cassette plate 30 have been lowered into association with the valve and sensor assembly 32. The illustrated valve and sensor assembly 32 includes valve actuators 36 and pressure-sensing actuators or transducers 38 configured to act in concert with the valve stations 26 and sensing stations 28 of the cassette 22 to direct and monitor fluid flow within the cassette 22. The valve actuators 36 and the pressure-sensing actuators or transducers 38 may be mutually arranged in the same layout as the valve stations 26 and sensing stations 28 on the bottom of the cassette 22.

The cassette holder 20 includes a pump mechanism or system configured to convey fluid through the pathways of the cassette 22. In the illustrated embodiment, the cassette holder 20 includes a plurality of peristaltic pumps 40a-40f. Each peristaltic pump 40 is configured to receive a different tubing loop 42 extending from a sidewall of the cassette 22 for moving fluid through the tubing loops 42 and, hence, through the pathways of the cassette 22 in fluid communication with the tubing loops 42, along with moving fluid through the various other components of the fluid flow circuit 14. The pump stations 40a-40f may perform different functions, depending on the configurations of the fluid processing device 12 and the fluid flow circuit 14 and the nature of the procedure to be performed. However, in an exemplary procedure in which blood is separated into a plasma constituent and a red blood cell constituent (with the plasma constituent subsequently being separated into platelet-poor plasma and platelet concentrate), one pump 40a is configured to convey anticoagulated blood to the separator, another pump 40b is configured to convey separated plasma back into the separator, a third pump 40c is configured to convey separated platelets through the fluid flow circuit 14, a fourth pump 40d is configured to convey a separated plasma constituent from the separator, a fifth pump 40e is configured to draw blood into the fluid flow circuit 14 from a source, and a sixth pump 40f is configured to add an anticoagulant fluid to the blood from the blood source.

In other embodiments, other pump mechanisms may be employed without departing from the scope of the present disclosure. For example, the cassette body may define one or more pump stations configured to be manipulated (e.g., by an actuator acting upon the flexible membrane overlaying the pump station) to convey fluid through the cassette 22 and the rest of the fluid flow circuit 14.

In addition to the cassette 22, the fluid flow circuit 14 includes a variety of conduits 44 placing the various components of the fluid flow circuit 14 into communication with each other. In the illustrated embodiment, each conduit 44 is provided as a length of tubing extending from one component of the fluid flow circuit 14 to another component or extending between two regions of a single component (as is the case with the tubing loops 42). In one embodiment, the conduits 44 are configured as lengths of tubing formed of a flexible material, such as plasticized polyvinyl chloride, but it should be understood that the conduits 44 may be variously configured without departing from the scope of the present disclosure.

Figure 3:
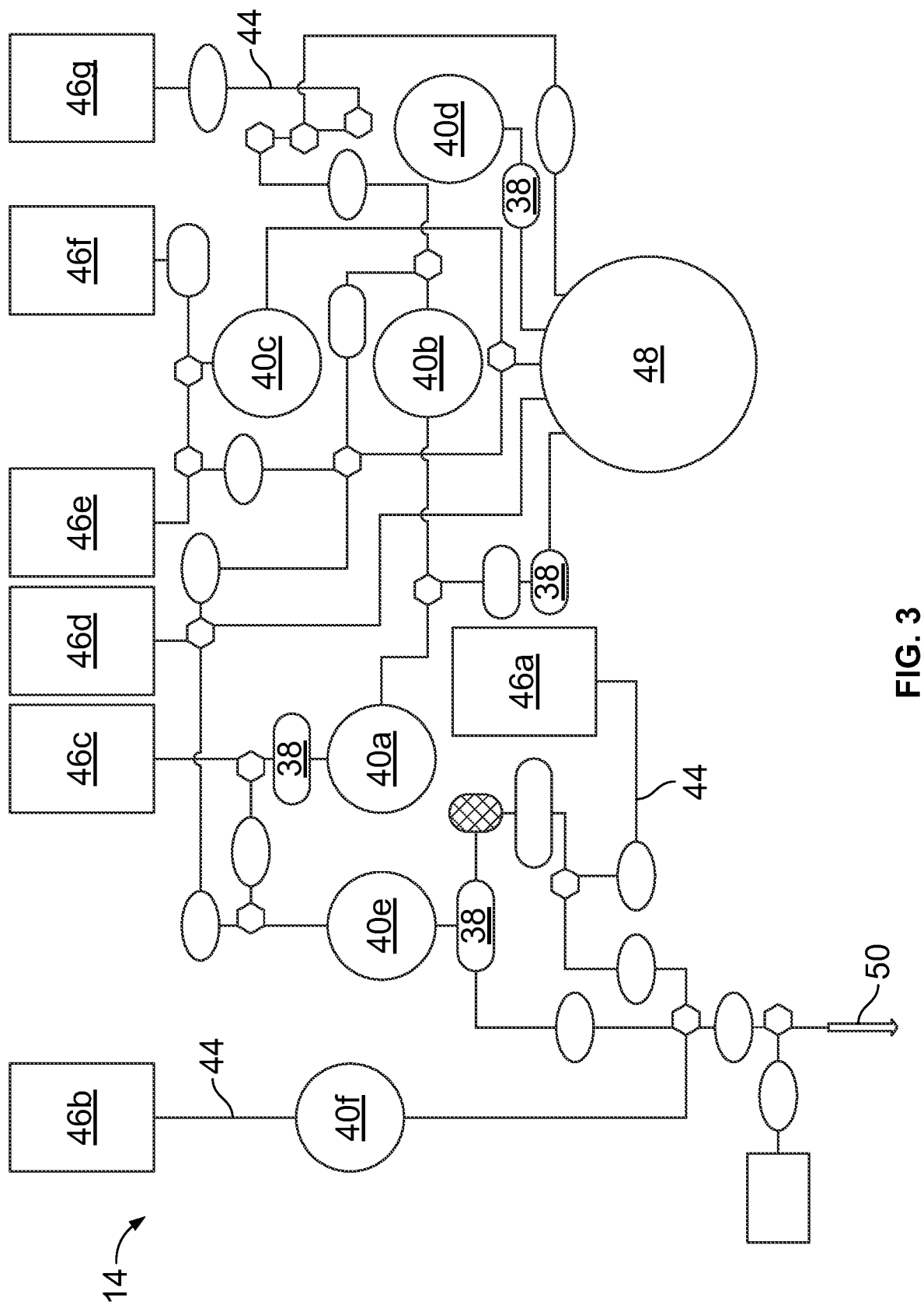
FIG. 3 is a schematic view of a fluid flow circuit of the fluid processing system of FIG. 1 mounted to the fluid processing device of FIG. 2.

The illustrated fluid flow circuit 14 includes a plurality of containers 46a-46g and a fluid separation chamber 48 (FIG. 3). The fluid separation chamber 48 is fluidly connected to the cassette 22 by a flexible umbilicus and configured to be received by the separator of the fluid processing device 12. The fluid separation chamber 48 is not illustrated in detail, but may be configured as described in greater detail in U.S. Pat. No. 10,561,784, which is hereby incorporated herein by reference and which also describes an exemplary centrifuge or separator that may be incorporated into the fluid processing device 12 and used in combination with the fluid separation chamber 48.

As for the containers 46a-46g, there may be any number of them and they may be variously configured, depending on the nature of the procedure to be executed by the fluid processing system 10. In the illustrated embodiment, in which blood is separated into three components, one of the containers 46a contains a priming fluid (e.g., saline), another container 46b contains an anticoagulant fluid, while a third container 46c is an "in process" container that temporarily receives blood during a separation procedure, allowing for blood separation while fluid is being returned to the blood source. One of the containers 46f contains an additive fluid, with the three remaining containers 46d, 46e, and 46g being collection containers configured to receive one or more separated blood components. This may include one of the containers 46 being treated as waste container, which receives fluids that are disposed of at the end of a procedure, rather than being retained for further use. The illustrated fluid processing device 12 is provided with a plurality of hangers 48 for supporting the containers 46a-46g. One or more of the hangers 48 may be provided with an associated weight scale to measure the weight of a container 46 supported by the hanger 48 and its contents.

Among the various containers, the fluid flow circuit 14 may include a source container configured to contain a fluid to be processed. In the case of blood separation or processing, this may include a source container configured as a blood pack. Alternatively, rather than providing a source container (and as illustrated in FIG. 3), one or more of the conduits 44 may be provided with a fluid source access device 50 configured to be connected or associated to a fluid source for conveying a fluid to be processed from the source into the fluid flow circuit 14. In the case of a blood processing procedure, a fluid source access device 50 may be configured as a phlebotomy needle to draw blood from a vein of a donor or patient. In any event, it should be understood that the fluid flow circuit 14 of FIGS. 1 and 3 is merely exemplary and differently configured fluid flow circuits may also be employed without departing from the scope of the present disclosure.

Regardless of the configuration of the fluid flow circuit 14 and the nature of the procedure to be executed by the fluid processing system 10, the various conduits 44 (and selected components) of the fluid flow circuit 14 must be primed prior to fluid processing. The procedure executed by the fluid processing system 10, including the priming phase, is carried out under the direction of a controller 52 of the fluid processing device 12, which controls and coordinates the operation of the other components of the fluid processing device 12 during a procedure. The controller 52 may be variously configured without departing from the scope of the present disclosure, provided that it is configured to coordinate the various tasks carried out by the components of the fluid processing device 12 during a fluid processing procedure. In one embodiment, the controller 52 may include a microprocessor (which, in fact may include multiple physical and/or virtual processors). According to other embodiments, the controller 52 may include one or more electrical circuits designed to carry out the actions described herein. In fact, the controller 52 may include a microprocessor and other circuits or circuitry. In addition, the controller 52 may include one or more memories. The instructions by which the microprocessor is programmed may be stored on the memory associated with the microprocessor, which memory/memories may include one or more tangible non-transitory computer readable memories, having computer executable instructions stored thereon, which when executed by the microprocessor, may cause the microprocessor to carry out one or more actions as described herein. In one exemplary embodiment, the controller 52 comprises a main processing unit (MPU), which can comprise, e.g., a PENTIUM® type microprocessor made by Intel Corporation, although other types of conventional microprocessors can be used.

Figure 7:
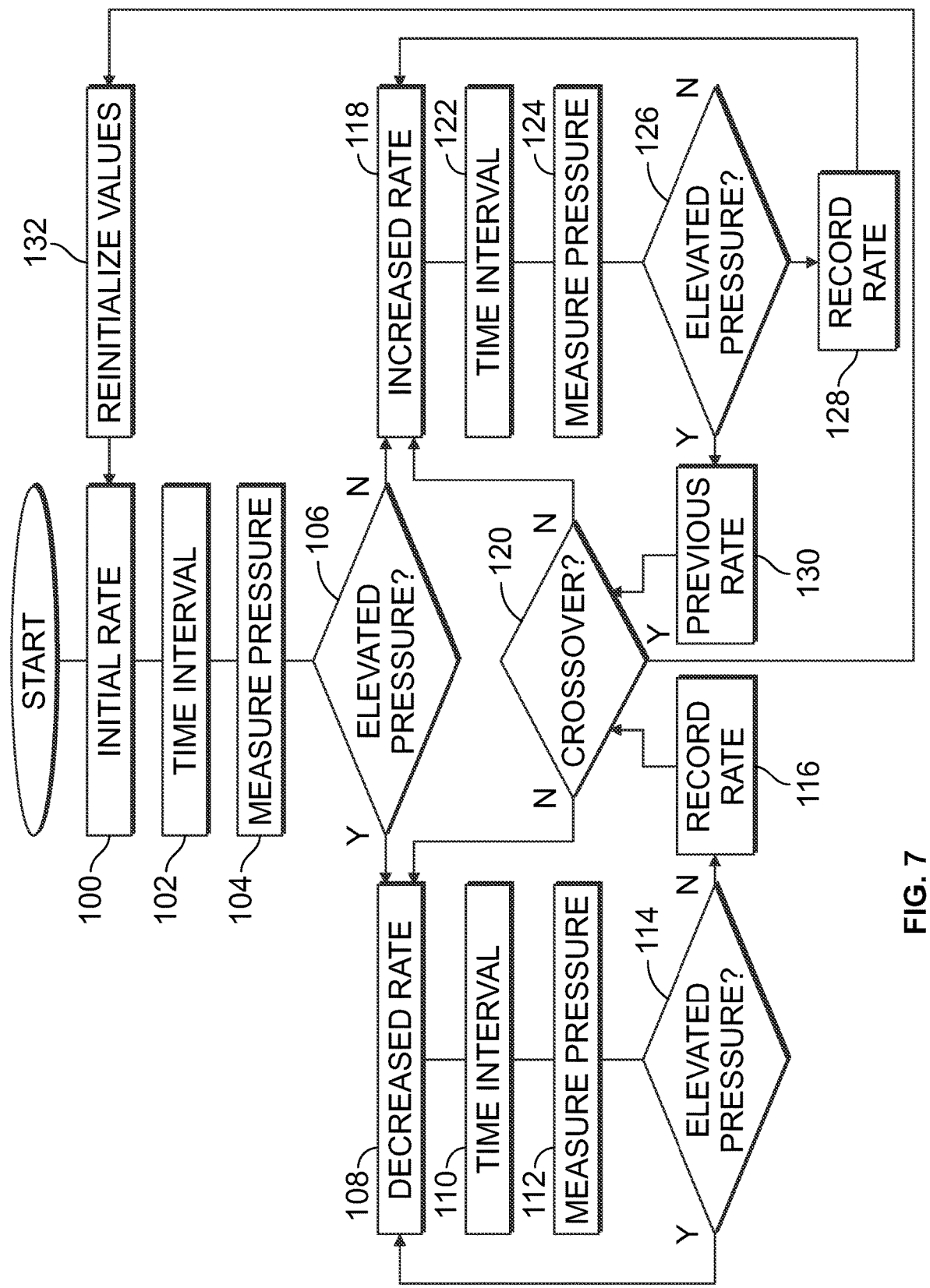
FIG. 7 is a flow chart showing a method for controlling the flow of fluid through a fluid flow circuit when priming the fluid flow circuit.

FIG. 7 illustrates an exemplary pressure-based protocol for adjusting fluid flow during a priming procedure that may be executed by the fluid processing system 10, under the direction of the controller 52. In short, two of the pumps 40a and 40e are controlled by the controller 52 to prime at least a portion of the fluid flow circuit 14 based on pressure measurements made by the valve and sensor assembly 32. One of the pumps 40a will be referred to herein as a "downstream pump" or "centrifuge pump" (though it should be understood that the procedure is not limited to use in combination with a fluid processing system 10 including a centrifuge or any particular separator), while the other pump 40*e* will be referred to herein as an "upstream pump" or "blood pump" (though it should be understood that the procedure is not limited to blood processing, but may be used when processing other biological and non-biological fluids).

The protocol illustrated in FIG. 7 is used to directly control only one of the pumps 40*e*, which is upstream of the other pump 40*a*. Rather than directly controlling the downstream pump 40*a*, the operational rate of the downstream pump 40*a* is instead dependent upon the operational rate of the upstream pump 40*e*. More particularly, the amount of priming fluid supplied to the portion of the fluid flow circuit 14 associated with the downstream pump 40*a* is directly related to the operational rate of the upstream pump 40*e*, with more priming fluid being supplied when the upstream pump 40*e* is operated at a relatively high rate. Thus, when the operational rate of the upstream pump 40*e* is increased, the operational rate of the downstream pump 40*a* may be correspondingly increased. It should be understood that this approach is not limited to systems having two pumps that are controlled during a priming procedure, but may be applied to systems having only one pump and systems having more than two pumps to be controlled during a priming procedure.

The valve and sensor assembly 32 is controlled by the controller 52 to direct the flow of a priming fluid through the fluid flow circuit 14, with any route taken by the priming fluid through the fluid flow circuit 14 being within the scope of the present disclosure. The controller 52 additionally controls the valve and sensor assembly 32 to monitor the pressure in a conduit or region of the fluid flow circuit 14. In the illustrated embodiment, the pressure in a conduit 44 positioned between the priming fluid container 46*a* and the upstream pump 40*e* is monitored by a pressure sensor 38 of the valve and sensor assembly 32 (FIG. 3). The pressure in this conduit 44 is indicative of any resistance to the flow of priming fluid from the container 46*a*, with elevated pressure being indicative of a blockage. In other embodiments, in which blood from a patient or donor is used to prime the circuit, the measured pressure will be indicative of the status of a vein of the patient or donor, with an elevated pressure being indicative of a possible vein collapse or other irregularity in blood draw.

Turning now to the priming procedure illustrated in FIG. 7, the upstream pump 40*e* is operated at a predetermined or preselected initial rate to convey priming fluid through at least a portion of the fluid flow circuit 14, including the conduit 44 being monitored by the valve and sensor assembly 32 (represented in FIG. 7 at 100). In one embodiment, the initial rate is set to what is considered to be an optimized or ideal operational rate, which will vary depending on any of a number of factors, including the configuration of the pump 40*e*, the configuration of the fluid flow circuit 14, and the composition of the priming fluid. However, it should be understood that the magnitude of the initial rate may vary without departing from the scope of the present disclosure, which may include employing an initial rate that is different from the optimized or ideal operational rate.

The pump 40*e* is operated at the initial rate for a predetermined or preselected time interval (represented in FIG. 7 at 102), While a time interval is employed in the illustrated embodiment, it should be understood that some other metric may be employed to measure the amount of time that the pump 40*e* has been operating at the initial rate (e.g., the number of revolutions or cycles executed by the pump 40*e* or the volume of fluid conveyed through the conduit 44 by the pump 40*e*). The exact duration of the time interval may vary without departing from the scope of the present disclosure, though it may be advantageous to employ a time interval that is sufficiently long to allow fluid flow through the conduit 44 to stabilize at the current operational rate and for any blockage or flow irregularity to present itself. It may also be advantageous to employ a time interval that is sufficiently short that the controller 52 is capable of reacting to a blockage or flow irregularity relatively quickly, rather than allowing the blockage or flow irregularity to persist longer than necessary.

The pressure measured by the pressure sensor 38 (represented in FIG. 7 at 104) is compared to a predetermined or maximum pressure at the end of the time interval (represented in FIG. 7 at 106). While the pressures are compared at the end of the time interval, it should be understood that the pressure sensor 38 will typically be monitoring the pressure in the conduit 44 during the entirety of the time interval and afterwards. The exact magnitude of the predetermined pressure may vary without departing from the scope of the present disclosure, with the predetermined pressure depending on various factors, including the nature and configurations of the upstream pump 40*e* and the conduit 44. While the exact magnitude of the predetermined pressure may vary, in general, when executing a blood prime using blood from a living source, it may be advantageous to employ a predetermined pressure having a relatively low magnitude to better protect the vein of the source.

It should be understood that the predetermined pressure may be any value, including positive values and negative values, which may depend on the configuration of the upstream pump 40*e* and the location of the pressure sensor 38. When a negative pressure is employed (which is typically the case when the priming fluid source is positioned upstream of the pump 40*e*, with the pressure sensor 38 positioned between the pump 40*e* and the priming fluid source, as in the embodiment of FIG. 3), a measured pressure that is more negative than the predetermined pressure will be indicative of a blockage or flow irregularity. On the other hand, when a positive pressure is employed (which may be the case when the pump 40*e* is positioned upstream of the priming fluid source), a measured pressure that is greater than the predetermined pressure will be indicative of a blockage or flow irregularity. Thus, it should be understood that the magnitude of the pressure measured by the pressure sensor 38 is compared to the magnitude of the predetermined pressure. If the magnitude of the measured pressure is less than the magnitude of the predetermined pressure (regardless of whether the pressures are positive or negative), it is indicative of flow through the conduit 44 being acceptable. If the magnitude of the measured pressure is greater than the magnitude of the predetermined pressure, it is indicative of a blockage or flow irregularity in the conduit 44.

When the initial rate is set to what is considered to be an optimized or ideal operational rate, it may be most typical for the magnitude of the measured pressure at the end of the time interval to be greater than the magnitude of the predetermined pressure (which may result, for example, from an imperfection in the fluid flow circuit 14 that prevents the pump 40*e* from operating at the ideal rate without creating a flow irregularity). In this case (which is represented in FIG. 7 as a "Y" arrow to the left of step 106), the controller 52 will reduce the operational rate of the pump 40*e* from the current rate to a decreased rate (represented in FIG. 7 at 108). The magnitude of the reduction in operational rate may vary without departing from the scope of the present disclosure, along with the magnitude of the decreased rate. The controller 52 may be preprogrammed with a suitable rate decrease increment and/or be programmed to allow an operator to select a rate decrease increment. The controller 52 may be further programmed with a minimum operational rate to prevent the pump 40e from being operated at an undesirably low rate.

In one embodiment, when the pump 40e is operating at the initial rate and the magnitude of the measured pressure is greater than the magnitude of the predetermined pressure at the end of the time interval, the decreased rate may be a predetermined "safe" rate. The "safe" rate may be an empirically determined value proven to resolve flow restrictions with a high degree of certainty. In other embodiments, the operational rate of the pump 40e may be reduced to some other decreased rate, rather than to the "safe" rate. For example, when step 108 is executed later during a priming procedure, the pump 40e may have previously been operated at at least one rate that did not result in an elevated pressure reading at the end of a timing interval. In this case, the controller 52 may command the pump 40e to operate at the most recent of these operational rates, which may be referred to herein as the "last good" rate (so called because it is the most recent rate at which the pump 40e was operated without resulting in an elevated pressure reading).

The pump 40e is operated at the decreased rate for a predetermined or preselected time interval (represented in FIG. 7 at 110). While a time interval is employed in the illustrated embodiment, it should be understood that some other metric may be employed to measure the amount of time that the pump 40e has been operating at the decreased rate (e.g., the number of revolutions or cycles executed by the pump 40e or the volume of fluid conveyed through the conduit 44 by the pump 40e).

The time interval employed in step 110 may be the same as used when operating the pump 40e at the initial rate (step 102) or may be different. For example, the duration of the time interval may depend on the magnitude of the decreased rate, such as with smaller time intervals being used with lower operational rates, on account of less time being required to ensure that flow conditions within the conduit 44 have stabilized. In another embodiment, the duration of the time interval may depend on the magnitude of the rate decrease increment, with larger time intervals being used with bigger changes (i.e., larger rate decrease increments) to better ensure that flow conditions have stabilized. In any event, the exact duration of the time interval may vary without departing from the scope of the present disclosure, though (as noted above) it may be advantageous to employ a time interval that is sufficiently long to allow fluid flow through the conduit 44 to stabilize at the current (decreased) operational rate and for any blockage or flow irregularity to present itself. As also noted above, it may also be advantageous to employ a time interval that is sufficiently short that the controller 52 is capable of reacting to a blockage or flow irregularity relatively quickly, rather than allowing the blockage or flow irregularity to persist longer than necessary.

The magnitude of the measured pressure at the end of the time interval (represented in FIG. 7 at 112) is compared to the magnitude of the predetermined pressure (represented in FIG. 7 at 114). When the magnitude of the measured pressure at the end of the time interval is still greater than the magnitude of the predetermined pressure (represented in FIG. 7 as a "Y" arrow to the left of step 114), the controller returns to step 108 and repeats the process of decreasing the operational rate of the pump 40e yet again (step 108), allowing the pump 40e to operate at the current (twice decreased) operational rate for a time interval (step 110), and then measuring the pressure in the conduit 44 (step 112) and comparing the magnitude of the measured pressure to the magnitude of the predetermined pressure (step 114). This process repeats until the magnitude of the measured pressure is less than the magnitude of the predetermined pressure (represented in FIG. 7 as an "N" arrow to the right of step 114). The magnitude of the rate decrease increment may be the same for each cycle or may be different, such as with the magnitude of the rate decrease increment getting smaller as the operational rate decreases (i.e., as the operational rate approaches either a minimum rate or an acceptable operational rate).

When the magnitude of the measured pressure at the end of a time interval is finally less than the magnitude of the predetermined pressure (represented in FIG. 7 as an "N" arrow to the right of step 114), the controller 52 records the current (decreased) operational rate as the "last good" rate (or most recent acceptable operational rate) at step 116 and moves on to step 118. As shown in FIG. 7 at 116, the controller 52 may also move directly to step 118 after operating the pump 40e at the initial rate when the magnitude of the measured pressure at the end of that initial time interval is less than the magnitude of the predetermined pressure (represented in FIG. 7 as an "N" arrow to the right of step 106). FIG. 7 illustrates a step 120 in which the controller 52 considers whether adjusted rates have "crossed over" each other before advancing from step 116 to step 118. This step 120 will be explained in greater detail below but, if the operational rate of the pump 40e was not previously increased during the priming procedure, the answer to the inquiry will be "no" and the controller 52 will advance to step 118 (as represented in FIG. 7 as an "N" arrow to the right of step 120).

Regardless of how the controller 52 arrives at step 118, in this step it will increase the operational rate of the pump 40e from the current rate to an increased rate. When moving directly from the initial time interval to step 118, the current rate will be the initial rate, whereas the current rate will instead be the "last good" rate recorded by the controller 52 at step 116 when the operational rate has first been reduced by the controller 52 in order to resolve a flow irregularity arising from operating the pump at the initial rate (i.e., after the controller 52 has executed the sequence of steps 108, 110, and 112 one or more times).

The magnitude of the increase in operational rate may vary without departing from the scope of the present disclosure, along with the magnitude of the increased rate. The controller 52 may be preprogrammed with a suitable rate increase increment and/or be programmed to allow an operator to select a rate increase increment. For example, the operator may be given the option of a "more aggressive" approach in which the rate increase increment is relatively high (to more quickly increase the operational rate of the pump 40e) or a "more conservative" approach in which the rate increase increment is relatively low (to more slowly increase the operational rate of the pump 40e). The controller 52 may be programmed with a maximum operational rate to prevent the pump 40e from being operated at an undesirably high rate.

The pump 40e is operated at the increased rate for a predetermined or preselected time interval (represented in FIG. 7 at 122). While a time interval is employed in the illustrated embodiment, it should be understood that some other metric may be employed to measure the amount of time that the pump 40e has been operating at the increased rate (e.g., the number of revolutions or cycles executed by the pump 40e or the volume of fluid conveyed through the conduit 44 by the pump 40e).

The time interval employed in step 122 may be the same as used when operating the pump 40e at the initial rate (step 102) or at a decreased rate (step 110) or may be different. For example, the duration of the time interval may depend on the magnitude of the increased rate, with larger time intervals being used with larger operational rates to better ensure that flow conditions within the conduit 44 have stabilized. In another embodiment, the duration of the time interval may depend on the magnitude of the rate increase increment, with larger time intervals being used with bigger changes (i.e., larger rate increase increments) to better ensure that flow conditions have stabilized. In any event, the exact duration of the time interval may vary without departing from the scope of the present disclosure, though (as noted above) it may be advantageous to employ a time interval that is sufficiently long to allow fluid flow through the conduit 44 to stabilize at the current (increased) operational rate and for any blockage or flow irregularity to present itself. As also noted above, it may also be advantageous to employ a time interval that is sufficiently short that the controller 52 is capable of reacting to a blockage or flow irregularity relatively quickly, rather than allowing the blockage or flow irregularity to persist longer than necessary.

The magnitude of the measured pressure at the end of the time interval (represented in FIG. 7 at 124) is compared to the magnitude of the predetermined pressure (represented in FIG. 7 at 126). When the magnitude of the measured pressure at the end of the time interval is less than the magnitude of the predetermined pressure (represented in FIG. 7 as an "N" arrow to the right of step 126), the controller 52 records the current (increased) operational rate as the "last good" (or most recent) operational rate (represented in FIG. 7 at 128), then returns to step 118 and repeats the process of increasing the operational rate of the pump 40e yet again (step 118), allowing the pump 40e to operate at the current (twice increased) operational rate for a time interval (step 122), and then measuring the pressure in the conduit 44 (step 124) and comparing the magnitude of the measured pressure to the magnitude of the predetermined pressure (step 126). This process repeats (with the controller updating the "last good" operational rate and then increasing the operational rate) until the magnitude of the measured pressure exceeds the magnitude of the predetermined pressure (represented in FIG. 7 as a "Y" arrow to the left of step 126). The magnitude of the rate increase increments may be the same for each cycle or may be different, such as with the magnitude of the rate increase increment getting smaller as the operational rate increases (i.e., as the operational rate approaches either a maximum rate or the ideal or optimal rate).

As shown in FIG. 7, the "last good" operational rate is not updated at the end of the last cycle because the magnitude of the measured pressure exceeds the magnitude of the predetermined pressure, meaning that the operational rate employed in the last cycle was not "good" (i.e., resulted in a condition indicative of a blockage or flow irregularity). By way of example, if the controller 52 executes the sequence of steps 118, 122, and 124 five times before arriving at an operational rate resulting in an elevated pressure reading, the operational rate employed during the fifth and final iteration (the current operational rate) will correspond to the operational rate of the pump 40e when first advancing to step 118 plus five rate increase increments. As that operational rate resulted in an elevated pressure reading, the "last good" rate when the controller 52 finally exits the sequence of steps 118, 122, and 124 will be equal to the operational rate of the pump 40e during the previous or next-to-last cycle (corresponding to the operational rate of the pump 40e when first advancing to step 118 plus four rate increase increments, in this example).

When the magnitude of the measured pressure at the end of a time interval finally exceeds the magnitude of the predetermined pressure (represented in FIG. 7 as a "Y" arrow to the left of step 126), the controller 52 next (at step 130) decreases the operational rate of the pump 40e to the "last good" rate recorded at step 128 and moves on to step 120. As referenced above, during step 120, the controller 52 considers whether adjusted rates have "crossed over" each other before advancing to the next step. If the operational rate of the pump 40e was not previously decreased during the priming procedure, the answer to the inquiry will be "no" and the controller 52 will advance to step 108 (as represented in FIG. 7 as an "N" arrow to the left of step 120). On the other hand, if the operational rate of the pump 40e has been previously decreased and increased during the priming procedure (regardless of whether the rate was first adjusted downwardly or upwardly), the controller 52 will compare the "last good" rate recorded at step 116 to the "last good" rate recorded at step 128.

As described above, the "last good" rate recorded at step 116 is arrived at by decreasing the operational rate of the pump 40e, while the "last good" rate recorded at step 128 is arrived at by increasing the operational rate of the pump 40e. Thus, the "last good" rate recorded at step 116 will be reflective of an overall decrease in the operational rate of the pump 40e (starting at a relatively high rate and decreasing the rate until it is sufficiently low), with the "last good" rate recorded at step 128 being reflective of an overall increase in the operational rate of the pump 40e (starting at a relatively low rate and increasing the rate until the predetermined pressure is exceeded at the end of a time interval). Accordingly, it may be said that the adjustments have "crossed" when the "last good" rate recorded at step 128 (i.e., the upward adjustment) is greater than the "last good" rate recorded at step 116 (i.e., the downward adjustment).

When there has been no "crossover," the controller 52 will advance the priming procedure from the most recently executed adjustment approach to the other adjustment approach, with the pump 40e operating at the most recently recorded "last good" rate. This entails either advancing from the "decreasing" adjustment sequence to the "increasing" adjustment sequence (as represented in FIG. 7 as an "N" arrow to the right of step 120) or advancing from the "increasing" adjustment sequence to the "decreasing" adjustment sequence (as represented in FIG. 7 as an "N" arrow to the left of step 120). This repeated alternation between the "increasing" adjustment sequence and the "decreasing" adjustment sequence can be understood as the controller 52 making the necessary adjustments to the operational rate of the pump 40e (i.e., decreasing the rate when the resulting pressure is too great and increasing the rate when the resulting pressure is acceptably low) so as to converge upon an optimized rate of operation of the pump 40e.

On the other hand, when there has been a "crossover" (represented in FIG. 7 as a "Y" arrow at the bottom of step 120) it is indicative of an overcorrection or over-adjustment of the operational rate of the pump 40e, rather than the controller 52 successfully converging upon an optimized rate of operation. This overcorrection or over-adjustment may be caused by any of a number of factors, such as a change in the nature of the fluid flow circuit 14 during the priming procedure. Regardless of the cause of the overcorrection or over-adjustment, the controller 52 will respond by reinitializing the "last good" rates (represented in FIG. 7 at 132) and returning to step 100, thus restarting the rate adjustment protocol illustrated in FIG. 7. The protocol of FIG. 7 may be repeated any of a number of times during a priming procedure, with the controller 52 ending the priming procedure when the fluid flow circuit 14 has been successfully primed (which may be determined by any of a number of approaches, such as measuring the amount of priming fluid that has been conveyed through the fluid flow circuit 14 by the pump 40*e*).

It should be understood that the protocol illustrated in FIG. 7 is merely exemplary and that additional steps may be incorporated into the protocol without departing from the scope of the present disclosure. For example, the controller 52 may be configured to automatically return to step 100 whenever the pump 40*e* is stopped during the priming procedure. If the pump 40*e* has been stopped, it may be indicative of a change in the nature of the fluid flow circuit 14, such that any previously established "last good" rate may no longer be applicable.

It should also be understood that increasing a pump rate upon determining that the magnitude of a measured pressure within a conduit is less than the magnitude of a predetermined pressure and decreasing a pump rate upon determining that the magnitude of the measured pressure is not less than the magnitude of that predetermined pressure (as described above and shown in FIG. 7) is only one possible approach, with the opposite approach also being within the scope of the present disclosure. Indeed, it may be advantageous to provide for a pump rate to be increased upon determining that the magnitude of a measured pressure within a conduit is greater than the magnitude of a predetermined pressure and for the pump rate to be decreased upon determining that the magnitude of the measured pressure is not greater than the magnitude of the predetermined pressure. The former approach (of FIG. 7) may be advantageous when pressure at a pump inlet is being monitored (because elevated pressure may be indicative of a blockage or flow irregularity), whereas the latter approach (which proceeds according to the above description of the approach of FIG. 7, except for a reversal to the responses to high- and low-magnitude pressure measurements) may be advantageous when pressure at a pump outlet is being monitored (because a lower magnitude pressure level may be indicative of a blockage or flow irregularity).

Regardless of the exact steps executed by the controller 52 in carrying out a pump control protocol according to the present disclosure, it will be seen that adjustments to the pump(s) are automatically implemented by the controller 52 in response to flow irregularity. This is an improvement upon conventional systems, which require operator oversight and intervention when a flow irregularity arises. For example, the controller of a conventional system may be configured to stop one or more pumps when a flow irregularity arises during a priming procedure. The operator is notified of the condition and instructed to take action to remedy the condition (e.g., by agitating a priming fluid container or adjusting the position of a phlebotomy needle in the vein of a patient or donor). Once the operator has taken the appropriate action(s), they notify the controller that the condition has been addressed, followed by the controller restarting the pump(s) and continuing the priming procedure. In addition to decreasing the amount of operator intervention, it will also be seen that a system executing a priming procedure according to the present disclosure (with automatic adjustment of the operational rate of one or more pumps) may be able to complete the priming procedure more quickly than a system executing a conventional priming procedure because a detected flow irregularity will result in a decrease in the operational rate of the pump(s), rather than the pump(s) being stopped to allow for manual intervention.

Aspects

Aspect 1. A fluid processing device configured for use in combination with a fluid flow circuit, the fluid processing device comprising: a pump; a pressure sensor; and a controller, wherein the controller is configured to execute a priming procedure including controlling the pump to operate at a current rate for a predetermined time interval to convey a priming fluid through at least a portion of a fluid flow circuit, controlling the pressure sensor to measure a pressure in a conduit of the fluid flow circuit, comparing the magnitude of the pressure to the magnitude of a predetermined pressure at the end of the predetermined time interval, and when the magnitude of the pressure is less than the magnitude of the predetermined pressure at the end of the predetermined time interval, controlling the pump to operate at an increased rate that is greater than the current rate, and when the magnitude of the pressure is not less than the magnitude of the predetermined pressure at the end of the predetermined time interval, controlling the pump to operate at a decreased rate that is less than the current rate, wherein when the pump has not previously been operated during the priming procedure at a previous rate at which the magnitude of the pressure was less than the magnitude of the predetermined pressure at the end of a previous time interval during which the pump was operated at said previous rate, the decreased rate is equal to a predetermined safe rate, and when the pump has previously been operated during the priming procedure at at least one previous rate at which the magnitude of the pressure was less than the magnitude of the predetermined pressure at the end of a previous time interval during which the pump was operated at said at least one previous rate, the decreased rate is equal to the previous rate at which the pump most recently operated at which the magnitude of the pressure was less than the magnitude of the predetermined pressure at the end of said previous time interval during which the pump was operated at said at least one previous rate during the priming procedure.

Aspect 2. The fluid processing device of Aspect 1, further comprising a second pump, wherein the controller is configured to control the second pump during the priming procedure to operate at a rate based at least in part on the rate at which the pump is operating.

Aspect 3. The fluid processing device of any one of the preceding Aspects, wherein the priming fluid comprises a non-biological fluid.

Aspect 4. The fluid processing device of any one of the preceding Aspects, wherein the priming fluid comprises a biological fluid.

Aspect 5. The fluid processing device of any one of the preceding Aspects, wherein the controller is configured to not control the pump to operate at a rate greater than a predetermined maximum rate during the priming procedure.

Aspect 6. The fluid processing device of any one of the preceding Aspects, wherein the controller is configured to not control the pump to operate at a rate less than a predetermined minimum rate during the priming procedure.

Aspect 7. The fluid processing device of any one of the preceding Aspects, wherein the predetermined pressure is greater than zero.

Aspect 8. The fluid processing device of any one of Aspects 1-6, wherein the predetermined pressure is less than zero.

Aspect 9. The fluid processing device of any one of the preceding Aspects, wherein the controller is configured to record the current rate as a first rate when the rate at which the pump is operated has been decreased so as to result in the pressure in the conduit at the end of a time interval during which the pump was operated at the current rate having a magnitude less than the predetermined pressure, record the current rate as a second rate when the rate at which the pump is operated has been increased without resulting in the pressure in the conduit at the end of a time interval during which the pump was operated at the current rate having a magnitude greater than the predetermined pressure, after having controlled the pump to operate at said decreased rate, compare the first rate to the second rate before controlling the pump to operate at said increased rate, control the pump to operate at said increased rate when the first rate is greater than the second rate, and control the pump to not operate at said increased rate when the second rate is greater than the first rate, and after having controlled the pump to operate at said increased rate, compare the first rate to the second rate before controlling the pump to operate at said decreased rate, control the pump to operate at said decreased rate when the first rate is greater than the second rate, and control the pump to not operate at said decreased rate when the second rate is greater than the first rate.

Aspect 10. The fluid processing device of any one of the preceding Aspects, wherein the controller is configured to repeatedly increase the rate at which the pump is operated when the magnitude of the pressure is less than the magnitude of the predetermined pressure at the end of one of said time intervals, and decrease the rate at which the pump is operated when the magnitude of the pressure is greater than the magnitude of the predetermined pressure at the end of one of said time intervals so as to converge at an optimized rate of operation for the pump.

Aspect 11. A method for executing a priming procedure in which a pump of a fluid processing device is operated to convey a priming fluid through at least a portion of a conduit, the method comprising: operating the pump at a current rate for a predetermined time interval to convey the priming fluid through said at least a portion of the conduit; measuring a pressure in the conduit; comparing the magnitude of the pressure to the magnitude of a predetermined pressure at the end of the predetermined time interval; and when the magnitude of the pressure is less than the magnitude of the predetermined pressure at the end of the predetermined time interval, operating the pump at an increased rate that is greater than the current rate, and when the magnitude of the pressure is not less than the magnitude of the predetermined pressure at the end of the predetermined time interval, operating the pump at a decreased rate that is less than the current rate, wherein when the pump has not previously been operated during the priming procedure at a previous rate at which the magnitude of the pressure was less than the magnitude of the predetermined pressure at the end of a previous time interval during which the pump was operated at said previous rate, the decreased rate is equal to a predetermined safe rate, and when the pump has previously been operated during the priming procedure at at least one previous rate at which the magnitude of the pressure was less than the magnitude of the predetermined pressure at the end of a previous time interval during which the pump was operated at said at least one previous rate, the decreased rate is equal to the previous rate at which the pump most recently operated at which the magnitude of the pressure was less than the magnitude of the predetermined pressure at the end of said previous time interval during which the pump was operated at said at least one previous rate during the priming procedure.

Aspect 12. The method of Aspect 11, further comprising operating a second pump, wherein the second pump is operated during the priming procedure at a rate based at least in part on the rate at which the pump is operating.

Aspect 13. The method of any one of Aspects, 11-12 wherein the priming fluid comprises a non-biological fluid.

Aspect 14. The method of any one of Aspects 11-13, wherein the priming fluid comprises a biological fluid.

Aspect 15. The method of any one of Aspects 11-14, wherein the pump is not operated at a rate greater than a predetermined maximum rate during the priming procedure.

Aspect 16. The method of any one of Aspects 11-15, wherein the pump is not operated at a rate less than a predetermined minimum rate during the priming procedure.

Aspect 17. The method of any one of Aspects 11-16, wherein the predetermined pressure is greater than zero.

Aspect 18. The method of any one of Aspects 11-16, wherein the predetermined pressure is less than zero.

Aspect 19. The method of any one of Aspects 11-18, further comprising recording the current rate as a first rate when the rate at which the pump is operated has been decreased so as to result in the pressure in the conduit at the end of a time interval during which the pump was operated at the current rate having a magnitude less than the predetermined pressure, recording the current rate as a second rate when the rate at which the pump is operated has been increased without resulting in the pressure in the conduit at the end of a time interval during which the pump was operated at the current rate having a magnitude greater than the predetermined pressure, after having operated the pump at said decreased rate, comparing the first rate to the second rate before operating the pump to operate at said increased rate, operating the pump at said increased rate when the first rate is greater than the second rate, and not operating the pump at said increased rate when the second rate is greater than the first rate, and after having operated the pump at said increased rate, comparing the first rate to the second rate before operating the pump at said decreased rate, operating the pump at said decreased rate when the first rate is greater than the second rate, and not operating the pump at said decreased rate when the second rate is greater than the first rate.

Aspect 20. The method of any one of Aspects 11-19, wherein the rate at which the pump is operated is repeatedly increased when the magnitude of the pressure is less than the magnitude of the predetermined pressure at the end of one of said time intervals, and decreased when the magnitude of the pressure is greater than the magnitude of the predetermined pressure at the end of one of said time intervals so as to converge at an optimized rate of operation for the pump.

Aspect 21. A fluid processing device configured for use in combination with a fluid flow circuit, the fluid processing device comprising: a pump; a pressure sensor; and a controller, wherein the controller is configured to execute a priming procedure including controlling the pump to operate at a current rate for a predetermined time interval to convey a priming fluid through at least a portion of a fluid flow circuit, controlling the pressure sensor to measure a pressure in a conduit of the fluid flow circuit, comparing the magnitude of the pressure to the magnitude of a predetermined pressure at the end of the predetermined time interval, and when the magnitude of the pressure is greater than the magnitude of the predetermined pressure at the end of the predetermined time interval, controlling the pump to operate at an increased rate that is greater than the current rate, and when the magnitude of the pressure is not greater than the magnitude of the predetermined pressure at the end of the predetermined time interval, controlling the pump to operate at a decreased rate that is less than the current rate, wherein when the pump has not previously been operated during the priming procedure at a previous rate at which the magnitude of the pressure was greater than the magnitude of the predetermined pressure at the end of a previous time interval during which the pump was operated at said previous rate, the decreased rate is equal to a predetermined safe rate, and when the pump has previously been operated during the priming procedure at at least one previous rate at which the magnitude of the pressure was greater than the magnitude of the predetermined pressure at the end of a previous time interval during which the pump was operated at said at least one previous rate, the decreased rate is equal to the previous rate at which the pump most recently operated at which the magnitude of the pressure was greater than the magnitude of the predetermined pressure at the end of said previous time interval during which the pump was operated at said at least one previous rate during the priming procedure.

Aspect 22. The fluid processing device of Aspect 21, further comprising a second pump, wherein the controller is configured to control the second pump during the priming procedure to operate at a rate based at least in part on the rate at which the pump is operating.

Aspect 23. The fluid processing device of any one of Aspects 21-22, wherein the priming fluid comprises a non-biological fluid.

Aspect 24. The fluid processing device of any one of Aspects 21-23, wherein the priming fluid comprises a biological fluid.

Aspect 25. The fluid processing device of any one of Aspects 21-24, wherein the controller is configured to not control the pump to operate at a rate greater than a predetermined maximum rate during the priming procedure.

Aspect 26. The fluid processing device of any one of Aspects 21-25, wherein the controller is configured to not control the pump to operate at a rate less than a predetermined minimum rate during the priming procedure.

Aspect 27. The fluid processing device of any one of Aspects 21-26, wherein the predetermined pressure is greater than zero.

Aspect 28. The fluid processing device of any one of Aspects 21-26, wherein the predetermined pressure is less than zero.

Aspect 29. The fluid processing device of any one of Aspects 21-28, wherein the controller is configured to record the current rate as a first rate when the rate at which the pump is operated has been decreased so as to result in the pressure in the conduit at the end of a time interval during which the pump was operated at the current rate having a magnitude greater than the predetermined pressure, record the current rate as a second rate when the rate at which the pump is operated has been increased without resulting in the pressure in the conduit at the end of a time interval during which the pump was operated at the current rate having a magnitude less than the predetermined pressure, after having controlled the pump to operate at said decreased rate, compare the first rate to the second rate before controlling the pump to operate at said increased rate, control the pump to operate at said increased rate when the first rate is greater than the second rate, and control the pump to not operate at said increased rate when the second rate is greater than the first rate, and after having controlled the pump to operate at said increased rate, compare the first rate to the second rate before controlling the pump to operate at said decreased rate, control the pump to operate at said decreased rate when the first rate is greater than the second rate, and control the pump to not operate at said decreased rate when the second rate is greater than the first rate.

Aspect 30. The fluid processing device of any one of Aspects 21-29, wherein the controller is configured to repeatedly increase the rate at which the pump is operated when the magnitude of the pressure is greater than the magnitude of the predetermined pressure at the end of one of said time intervals, and decrease the rate at which the pump is operated when the magnitude of the pressure is less than the magnitude of the predetermined pressure at the end of one of said time intervals so as to converge at an optimized rate of operation for the pump.

Aspect 31. A method for executing a priming procedure in which a pump of a fluid processing device is operated to convey a priming fluid through at least a portion of a conduit, the method comprising: operating the pump at a current rate for a predetermined time interval to convey the priming fluid through said at least a portion of the conduit; measuring a pressure in the conduit; comparing the magnitude of the pressure to the magnitude of a predetermined pressure at the end of the predetermined time interval; and when the magnitude of the pressure is greater than the magnitude of the predetermined pressure at the end of the predetermined time interval, operating the pump at an increased rate that is greater than the current rate, and when the magnitude of the pressure is not greater than the magnitude of the predetermined pressure at the end of the predetermined time interval, operating the pump at a decreased rate that is less than the current rate, wherein when the pump has not previously been operated during the priming procedure at a previous rate at which the magnitude of the pressure was greater than the magnitude of the predetermined pressure at the end of a previous time interval during which the pump was operated at said previous rate, the decreased rate is equal to a predetermined safe rate, and when the pump has previously been operated during the priming procedure at at least one previous rate at which the magnitude of the pressure was greater than the magnitude of the predetermined pressure at the end of a previous time interval during which the pump was operated at said at least one previous rate, the decreased rate is equal to the previous rate at which the pump most recently operated at which the magnitude of the pressure was less than the magnitude of the predetermined pressure at the end of said previous time interval during which the pump was operated at said at least one previous rate during the priming procedure.

Aspect 32. The method of Aspect 31, further comprising operating a second pump, wherein the second pump is operated during the priming procedure at a rate based at least in part on the rate at which the pump is operating.

Aspect 33. The method of any one of Aspects 31-32, wherein the priming fluid comprises a non-biological fluid.

Aspect 34. The method of any one of Aspects 31-33, wherein the priming fluid comprises a biological fluid.

Aspect 35. The method of any one of Aspects 31-34, wherein the pump is not operated at a rate greater than a predetermined maximum rate during the priming procedure.

Aspect 36. The method of any one of Aspects 31-35, wherein the pump is not operated at a rate less than a predetermined minimum rate during the priming procedure.

Aspect 37. The method of any one of Aspects 31-36, wherein the predetermined pressure is greater than zero.

Aspect 38. The method of any one of Aspects 31-36, wherein the predetermined pressure is less than zero.

Aspect 39. The method of any one of Aspects 31-38, further comprising recording the current rate as a first rate when the rate at which the pump is operated has been decreased so as to result in the pressure in the conduit at the end of a time interval during which the pump was operated at the current rate having a magnitude greater than the predetermined pressure, recording the current rate as a second rate when the rate at which the pump is operated has been increased without resulting in the pressure in the conduit at the end of a time interval during which the pump was operated at the current rate having a magnitude less than the predetermined pressure, after having operated the pump at said decreased rate, comparing the first rate to the second rate before operating the pump to operate at said increased rate, operating the pump at said increased rate when the first rate is greater than the second rate, and not operating the pump at said increased rate when the second rate is greater than the first rate, and after having operated the pump at said increased rate, comparing the first rate to the second rate before operating the pump at said decreased rate, operating the pump at said decreased rate when the first rate is greater than the second rate, and not operating the pump at said decreased rate when the second rate is greater than the first rate.

Aspect 40. The method of any one of Aspects 31-39, wherein the rate at which the pump is operated is repeatedly increased when the magnitude of the pressure is greater than the magnitude of the predetermined pressure at the end of one of said time intervals, and decreased when the magnitude of the pressure is less than the magnitude of the predetermined pressure at the end of one of said time intervals so as to converge at an optimized rate of operation for the pump.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A fluid processing device configured for use in combination with a fluid flow circuit, the fluid processing device comprising:
  a pump;
  a pressure sensor; and
  a controller, wherein the controller is configured to execute a priming procedure including
    controlling the pump to operate at a current rate for a predetermined time interval to convey a priming fluid through at least a portion of the fluid flow circuit,
    controlling the pressure sensor to measure a pressure in a conduit of the fluid flow circuit,
    comparing of the pressure to of a predetermined pressure at the end of the predetermined time interval, and
    when of the pressure is less than the predetermined pressure at the end of the predetermined time interval, controlling the pump to operate at an increased rate that is greater than the current rate, and
    when the pressure is not less than the predetermined pressure at the end of the predetermined time interval, controlling the pump to operate at a decreased rate that is less than the current rate, wherein
      if the pump has not been operated at a previous rate during the priming procedure wherein the pressure was less than the predetermined pressure at the end of a previous time interval during which the pump was operated at said previous rate, the decreased rate is equal to a predetermined safe rate, and
      if the pump has been operated at at least one previous rate during the priming procedure wherein the pressure was less than the predetermined pressure at the end of a previous time interval when the pump was operated at said at least one previous rate, the decreased rate is equal to the previous rate at which the pump most recently operated at during the priming procedure when the pressure was less than the predetermined pressure at the end of said previous time interval when the pump was operated at said at least one previous rate.

2. The fluid processing device of claim 1, further comprising a second pump, wherein the controller is configured to control the second pump during the priming procedure to operate at a rate based at least in part on the rate at which the pump is operating.

3. The fluid processing device of claim 1, wherein the priming fluid comprises a non-biological fluid.

4. The fluid processing device of claim 1, wherein the priming fluid comprises a biological fluid.

5. The fluid processing device of claim 1, wherein the controller is configured to not control the pump to operate at a rate greater than a predetermined maximum rate during the priming procedure.

6. The fluid processing device of claim 1, wherein the controller is configured to not control the pump to operate at a rate less than a predetermined minimum rate during the priming procedure.

7. The fluid processing device of claim 1, wherein the predetermined pressure is greater than zero.

8. The fluid processing device of claim 1, wherein the predetermined pressure is less than zero.

9. The fluid processing device of claim 1, wherein the controller is configured to
  record the current rate as a first rate when the rate at which the pump is operated has been decreased so as to result in the pressure in the conduit at the end of a time interval during which the pump was operated at the current rate being less than the predetermined pressure,
  record the current rate as a second rate when the rate at which the pump is operated has been increased without resulting in the pressure in the conduit at the end of a time interval during which the pump was operated at the current rate being greater than the predetermined pressure,
  after having controlled the pump to operate at said decreased rate, compare the first rate to the second rate before controlling the pump to operate at said increased rate, control the pump to operate at said increased rate when the first rate is greater than the second rate, and control the pump to not operate at said increased rate when the second rate is greater than the first rate, and
  after having controlled the pump to operate at said increased rate, compare the first rate to the second rate before controlling the pump to operate at said decreased rate, control the pump to operate at said decreased rate when the first rate is greater than the second rate, and control the pump to not operate at said decreased rate when the second rate is greater than the first rate.

10. The fluid processing device of claim 1, wherein the controller is configured to repeatedly
increase the rate at which the pump is operated when the pressure is less than the predetermined pressure at the end of one of said time intervals, and
decrease the rate at which the pump is operated when the pressure is greater than the predetermined pressure at the end of one of said time intervals so as to converge at an optimized rate of operation for the pump.

11. A method for executing a priming procedure in which a pump of a fluid processing device is operated by a controller to convey a priming fluid through at least a portion of a conduit, the controller-implemented method comprising:
operating the pump at a current rate for a predetermined time interval to convey the priming fluid through said at least a portion of the conduit;
measuring a pressure in the conduit;
comparing the pressure to a predetermined pressure at the end of the predetermined time interval; and
when the pressure is less than the predetermined pressure at the end of the predetermined time interval, operating the pump at an increased rate that is greater than the current rate, and
when the pressure is not less than the predetermined pressure at the end of the predetermined time interval, operating the pump at a decreased rate that is less than the current rate, wherein
if the pump has not been operated at a previous rate during the priming procedure wherein the pressure was less than the predetermined pressure at the end of a previous time interval during which the pump was operated at said previous rate, the decreased rate is equal to a predetermined safe rate, and
if the pump has been operated at at least one previous rate during the priming procedure wherein the pressure was less than the predetermined pressure at the end of a previous time interval when the pump was operated at said at least one previous rate, the decreased rate is equal to the previous rate at which the pump most recently operated at during the priming procedure when the pressure was less than the predetermined pressure at the end of said previous time interval when the pump was operated at said at least one previous rate.

12. The method of claim 11, further comprising operating a second pump, wherein the second pump is operated during the priming procedure at a rate based at least in part on the rate at which the pump is operating.

13. The method of claim 11, wherein the priming fluid comprises a non-biological fluid.

14. The method of claim 11, wherein the priming fluid comprises a biological fluid.

15. The method of claim 11, wherein the pump is not operated at a rate greater than a predetermined maximum rate during the priming procedure.

16. The method of claim 11, wherein the pump is not operated at a rate less than a predetermined minimum rate during the priming procedure.

17. The method of claim 11, wherein the predetermined pressure is greater than zero.

18. The method of claim 11, wherein the predetermined pressure is less than zero.

19. The method of claim 11, further comprising
recording the current rate as a first rate when the rate at which the pump is operated has been decreased so as to result in the pressure in the conduit at the end of a time interval during which the pump was operated at the current rate being less than the predetermined pressure,
recording the current rate as a second rate when the rate at which the pump is operated has been increased without resulting in the pressure in the conduit at the end of a time interval during which the pump was operated at the current rate being greater than the predetermined pressure,
after having operated the pump at said decreased rate, comparing the first rate to the second rate before operating the pump to operate at said increased rate, operating the pump at said increased rate when the first rate is greater than the second rate, and not operating the pump at said increased rate when the second rate is greater than the first rate, and
after having operated the pump at said increased rate, comparing the first rate to the second rate before operating the pump at said decreased rate, operating the pump at said decreased rate when the first rate is greater than the second rate, and not operating the pump at said decreased rate when the second rate is greater than the first rate.

20. The method of claim 11, wherein the rate at which the pump is operated is repeatedly
increased when the pressure is less than the predetermined pressure at the end of one of said time intervals, and
decreased when the pressure is greater than the predetermined pressure at the end of one of said time intervals so as to converge at an optimized rate of operation for the pump.

* * * * *